United States Patent
Haley et al.

(10) Patent No.: US 8,865,133 B2
(45) Date of Patent: Oct. 21, 2014

(54) BI-LAYER PRESSED POWDERS ORAL ADHERING TABLET WITH ACACIA GUM ADHESIVE

(75) Inventors: Jeffrey T Haley, Bellevue, WA (US); Steven Edwards, Laguna Niguel, CA (US)

(73) Assignee: OraHealth Corporation, Bellevue, WA (US)

( * ) Notice: Subject to any disclaimer, the term of this patent is extended or adjusted under 35 U.S.C. 154(b) by 659 days.

(21) Appl. No.: 11/800,381

(22) Filed: May 4, 2007

(65) Prior Publication Data

US 2007/0274927 A1   Nov. 29, 2007

Related U.S. Application Data

(60) Provisional application No. 60/808,035, filed on May 23, 2006, provisional application No. 60/879,846, filed on Jan. 11, 2007, provisional application No. 60/887,595, filed on Feb. 22, 2007.

(51) Int. Cl.
| | | |
|---|---|---|
| *A61K 9/68* | (2006.01) | |
| *A61K 9/28* | (2006.01) | |
| *A61K 9/00* | (2006.01) | |
| *A61K 9/20* | (2006.01) | |

(52) U.S. Cl.
CPC ............. *A61K 9/0056* (2013.01); *A61K 9/2018* (2013.01); *A61K 9/2086* (2013.01); *A61K 9/006* (2013.01)
USPC .............. 424/48; 424/440; 424/441; 426/454

(58) Field of Classification Search
USPC ............ 426/285, 424; 424/471, 468, 473, 48, 424/440, 441; 3/285, 424
See application file for complete search history.

(56) References Cited

U.S. PATENT DOCUMENTS

| | | | |
|---|---|---|---|
| 4,059,686 A | 11/1977 | Tanaka | |
| 4,292,299 A * | 9/1981 | Suzuki et al. | 424/435 |
| 5,236,713 A | 8/1993 | Wato | |
| 5,330,761 A | 7/1994 | Baichwal | |
| 5,380,530 A * | 1/1995 | Hill | 424/440 |
| 5,578,315 A | 11/1996 | Chien | |
| 6,210,699 B1 | 4/2001 | Acharya | |
| 6,294,200 B1 * | 9/2001 | Conte et al. | 424/472 |
| 6,303,147 B1 | 10/2001 | Gilis | |
| 6,358,525 B1 * | 3/2002 | Guo et al. | 424/464 |
| 6,365,185 B1 | 4/2002 | Ritschel et al. | |
| 6,528,069 B1 | 3/2003 | Lefevre et al. | |
| 6,723,304 B2 | 4/2004 | Stiler | |
| 2003/0003140 A1 * | 1/2003 | Domb et al. | 424/449 |
| 2003/0031744 A1 * | 2/2003 | Cecil | 425/107 |
| 2003/0175360 A1 * | 9/2003 | Luzzatti | 424/653 |
| 2003/0219479 A1 | 11/2003 | Chen | |
| 2004/0062804 A1 * | 4/2004 | Lee et al. | 424/471 |
| 2004/0175428 A1 * | 9/2004 | Appel et al. | 424/473 |
| 2004/0241223 A1 * | 12/2004 | Wong | 424/464 |
| 2004/0247677 A1 * | 12/2004 | Oury et al. | 424/472 |
| 2004/0253307 A1 | 12/2004 | Hague et al. | |
| 2006/0093560 A1 * | 5/2006 | Chen et al. | 424/48 |
| 2006/0099257 A1 * | 5/2006 | Langridge et al. | 424/472 |
| 2006/0193909 A1 * | 8/2006 | Stawski et al. | 424/464 |
| 2007/0048369 A1 | 3/2007 | Foreman | |

OTHER PUBLICATIONS

NPL Pizza retrieved on Jan 5, 2014.*
ISR, Oct. 18, 2007.
University of the Sciences in Philadelphia; Remington: The Science and Practice of Pharmacy. 20th ed.; Baltimore: Lippincott Williams & Wilkins, 2000, pp. 858-893.

* cited by examiner

*Primary Examiner* — Humera Sheikh
*Assistant Examiner* — Bhaskar Mukhopadhyay

(57) ABSTRACT

A bi-layer, oral adhering tablet (troche) made by pressing powders with a bi-layer tablet press, having greater than 80% acacia gum as an adhesive in an adhering layer. In a preferred embodiment, the tablet has about 99% acacia gum.

12 Claims, 1 Drawing Sheet

BI-LAYER PRESSED POWDERS ORAL ADHERING TABLET WITH ACACIA GUM ADHESIVE

This application is a continuation in part of U.S. regular application Ser. No. 11/800,381 filed May 4, 2007 and claims priority from U.S. provisional patent applications 60/808,035 filed 23 May 2006 60/879,846 filed 11 Jan. 2007, and 60/887,595 filed 22 Feb. 2007.

BACKGROUND

Oral care researchers have established that frequent delivery of xylitol molecules in the mouth can reduce caries, gingivitis, periodontitis, halitosis and inner ear infections by suppressing the growth of certain bacteria. These bacteria thrive on certain carbohydrate molecules such as sucrose, glucose, fructose and other sugars but, when they ingest the xylitol molecules, they cease proliferating and cease to adhere to human tissues. Delivering xylitol molecules in the mouth also provides other benefits, such as remineralization of teeth and reduction of plaque and halitosis by stimulating saliva flow.

For these reasons, chewing gum, lozenges, and lollipops have been developed that have high levels of xylitol. These products are sold to consumers with instructions to keep the gum or candy in their mouths over time, so long as xylitol is being released, but this is typically less than five minutes for chewing gum and less than 15 minutes for lozenges and lollipops.

Mints, lozenges, and lollipops may be technically described as "troches". For treatment of health problems in the mouth or throat, people have for centuries held in their mouths a composition containing medication for topical application. Since the middle ages, the name for such a composition, derived from Latin and previously from Greek, is "troche". A modern form of troche is the cough drop, so named because it was formed by "dropping" hot, viscous, sugar-based candy onto a sheet or into a mold where it cools to form the troche. Another modern form of troche is the "lozenge", so named because it was in the shape of a diamond (like on playing cards), which is the meaning of the word "lozenge". A troche is large enough that a person is able to track where it is in the mouth and move it with their tongue, that is, larger than about 5 mm in at least two dimensions. Xylitol troches dissolve quickly and are insignificantly adherent in a human mouth.

For release of xylitol in the mouth over time, some people will prefer chewing gum and some people will prefer a troche, such as a lozenge or lollipop. There is a need for a third alternative, an adherent troche that will remain adhered to a spot in the mouth, such as a tooth, while the troche dissolves releasing xylitol or a similar polyol. And there is a need to slow the rate of dissolution to maintain therapeutic levels of xylitol or other polyol in the fluids of the oral cavity over longer periods of time.

U.S. Patent 6,139,861 issued to Mark Friedman surveys methods for adhering a troche to a location within the mouth. These methods include two forms of adherent troches, referred to by Friedman as a "mucoadhesive erodible tablet". These tablets are formed using polymers carboxymethylcellulose, hydroxymethylcellulose, polyacrylic acid, and carbopol-934. Another form of adherent troche is a flexible device, often called an "oral patch." Examples include the adherent, soluble oral patch disclosed by the same inventor in U.S. patent application Ser. No. 10/287,843 filed Nov. 5, 2002, which is incorporated herein by this reference, and multi-layer patches, such as those disclosed in PCT patent application serial number PCT/US2007/005947 (applicant reference 0795-030-04) by the same inventor entitled Multi-layer medical patch with impermeable center filed Mar. 7, 2007 which is incorporated herein by this reference.

SUMMARY OF THE INVENTION

In one aspect, the invention is a composition of predominantly solid phase polyol molecules, particularly xylitol, with a reduced rate of dissolution in saliva. The composition dissolves much more slowly than substantially pure (greater than or equal to 98%) xylitol or xylitol with flavors added. The composition is comprised of crystallized polyol molecules intermixed with molecules of hydrophilic gums that swell when exposed to water. By their binding to water molecules and swelling, the gum molecules block the flow of water to the polyol molecules and slow dissolution. The molecules of hydrophilic gums may be one or more of any of cellulose gum, including carboxymethylcellulose, methylcellulose, and hydroxypropylmethylcellulose, any of the other synthetic hydrophilic gums such as carbopol, polyvinyl acid, and polyacrylic acid, any hydrophilic natural vegetable gum such as xanthan gum, konjac gum, tara gum, gellan gum, locust bean gum, acacia gum, alginate, carrageenan, agar, and pectin, or a hydrophilic protein gum such as gelatin. Instead of xylitol, the polyol molecules may be any polyol that is a solid at room temperatures, such as erythritol, sorbitol, mannitol, maltitol, isomalt, and lactitol.

The composition may be formed by melting the polyol, dissolving the hydrophilic gums into the melted polyol, and then cooling the composition until the polyol molecules crystallize. Alternatively, it may be formed by pressing powders of polyol crystals and one or more gums into a tablet with a tablet press such that the composition will have polyol crystals as large as grains of powder and the molecules of hydrophilic gums are one or more of intermixed within the grains or a coating on the grains or clumped into their own grains as large as grains of powder. The composition may be formed into a troche, including a troche with a handle to form a lollipop or child's pacifier. In an embodiment, the dissolution time of the troche in a human mouth is, on average, more than 25 minutes. Alternatively, to achieve slow release of polyol molecules when added to other products held in the mouth, such as chewing gum, the composition may be formed into grains suitable for mixing into other foods, particularly foods with low water levels so that the grains do not dissolve into the foods. A chewing gum embodiment may be made by coating fine grains of xylitol with 2.5% - 6% carboxymethylcellulose (CMC) (by weight relative to the xylitol) and incorporating these grains into a chewing gum with insignificant amounts of water so the CMC remains un-hydrated until the gum is chewed.

In another aspect, the invention is an adherent troche, at least 5 mm in each of at least two dimensions, that, when held in a human mouth, remains in the mouth as a single item that will not spread to be in a plurality of locations in the mouth at one time and erodes, thereby releasing polyol molecules over time. The troche may be flexible, in which case it might be called a patch, or it might be rigid, such as a rigid pressed powder adherent tablet. In one embodiment, the troche comprises, by dry weight between 50% and 90% solid phase polyol molecules and between 10% and 50% adhesive molecules that adhere in a human mouth. In an embodiment, the polyol molecules are xylitol. Alternatively, the polyol molecules may comprise one or more of erythritol, sorbitol, mannitol, maltitol, isomalt, and lactitol.

The adhesive molecules may comprise acacia gum. Alternatively, they may comprise one or more of gelatin, alginate, starch, pectin, polyvinylpyrolidone, carboxymethylcellulose, hydroxymethylcellulose, polyvinyl acid, polyacrylic acid, and carbopol.

The troche may include a composition of polyol molecules intermixed with molecules of hydrophilic gums that swell when exposed to water as specified above. The troche may comprise two layers, a first layer comprised of, by dry weight, at least 75% solid phase polyol molecules and a second layer comprised of, by dry weight, at least 30% adhesive molecules.

In another aspect, the invention is an adherent troche that uses acacia gum (aka gum arabic) as the adhesive. The troche has a planar shape with a width greater than 5 mm and a thickness less than the width. One side of the thickness comprises, by dry weight, at least 50% acacia gum. The acacia gum adheres very well to teeth and gums.

The portion of the troche that includes the side with acacia gum may be formed by pressing powders into a tablet with a tablet press. The rest of the troche may be formed by adhering another layer to the acacia gum layer. In a preferred embodiment, the troche is a bi-layer tablet and a first layer which includes the first side comprises at least 80% acacia gum. Alternatively, the side with acacia gum may be formed by mixing the acacia gum into a paste with a solvent, forming a blob with the paste, and then removing most of the solvent to form a planar shape. The solvent may be water.

In another aspect, the invention is a method for making a rounded bi-layer oral adhesive tablet by configuring a bi-layer tablet press having a die and lower and upper punches such that the lower punch is dish shaped to produce a rounded tablet surface and the upper punch is substantially flat. One makes tablets with the press by first pouring into the die a granular material that is not intended to be oral adhesive, then tamping the granular material with the upper punch, then adding to the die oral adhesive granular material, then compressing the granular materials between the two punches to form a tablet that is substantially flat on an oral adhesive side and rounded on the other side.

The dish shape may be approximately a portion of a sphere. The dish shape may be produced by a face on a lower punch that is substantially flat in a center area and the center area is surrounded by a raised edge which forms a dish shape.

In another aspect, the invention is a method for combating bacterial effects in the oral-nasal cavities by providing dissolving troches comprising crystalline xylitol which, when exposed to saliva in a human mouth, on average, release xylitol molecules more slowly than a troche of substantially pure xylitol (greater than 98% purity) and instructing consumers of the troches to place a troche in a mouth and keep it there until the xylitol in the troche is dissolved. In one embodiment, the dissolution time of the troches in a human mouth is, on average, more than 25 minutes at typical mid day levels of saliva flow. The bacterial effects combated may comprise oral malodor, inner ear infections, gum infections, caries, plaque, sinus infections, or risk of Streptococcus mutans passing from the oral cavities into the blood.

In another aspect, the invention is a method for combating sinus infections by providing dissolving objects comprising crystalline xylitol and instructing consumers of the objects to place an object in the mouth and keep it there until the xylitol in the object is dissolved. The object may be chewing gum or a troche. When exposed to saliva in a human mouth, the troches might dissolve at about the same speed as pure xylitol or, on average, release xylitol molecules more slowly than a troche of pure xylitol. Preferably, the dissolution time of the troches in a human mouth is, on average, more than 25 minutes at typical mid day levels of saliva flow.

In another aspect, the invention is a method for combating cardiovascular disease by providing dissolving objects comprising crystalline xylitol and instructing consumers of the objects to place an object in the mouth and keep it there until the xylitol in the object is dissolved. The object may be chewing gum or a troche. When exposed to saliva in a human mouth, the troches might dissolve at about the same speed as pure xylitol or, on average, release xylitol molecules more slowly than a troche of pure xylitol. Preferably, the dissolution time of the troches in a human mouth is, on average, more than 25 minutes at typical mid day levels of saliva flow.

DETAILED DESCRIPTION

Figure 1:
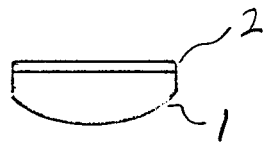
FIG. 1 shows a side view or cross section of a bi-layer adherent troche made with a tablet press.

The composition of predominantly solid phase polyol molecules, particularly xylitol, with a reduced rate of dissolution in saliva is made by mixing polyol molecules with substantial amounts of molecules of a hydrophilic gum that swell when exposed to water. The molecules of hydrophilic gums may be one or more of any of cellulose gum, including carboxymethylcellulose (CMC), methylcellulose, and hydroxypropylmethylcellulose, any of the other synthetic hydrophilic gums such as carbopol, polyvinyl acid, and polyacrylic acid, any hydrophilic natural vegetable gum such as xanthan gum, konjac gum, tara gum, gellan gum, locust bean gum, acacia gum, alginate, carrageenan, agar, and pectin, or a hydrophilic protein gum such as gelatin. For a xylitol troche, low viscosity CMC at about 3.4% is preferred. Instead of xylitol, the polyol molecules may be any polyol that is solid at room temperatures, such as erythritol, sorbitol, mannitol, maltitol, isomalt, and lactitol.

In one embodiment, the composition is formed by melting the polyol, dissolving the hydrophilic gums into the melted polyol, depositing blobs onto a sheet or into a mold, and then cooling the composition such that the polyol molecules are allowed to crystallize. Xylitol melts at about the boiling temperature of water. A double boiler with water and an additive that raises the boiling temperature, such as salt or propylene glycol, is effective and prevents over heating.

For this melted polyol embodiment, Xanthan gum at 5 to 9% is effective as the gum. A 0.8 gram blob at least twice as wide as thick lasted 70 minutes dissolving in the mouth. Xanthan with konjac gum is equally effective. The gums dissolve quite slowly in the hot liquid xylitol. On a magnetic stirrer hot plate, one hour can be required to achieve stasis of dissolution. High viscosity carboxymethylcellulose (CMC 15000from TIC Gums) required only 2.4% to be effective. A preferred embodiment has 3.4% low viscosity carboxymethylcellulose (CMC 15 from TIC Gums) and 96.6% xylitol.

Gelatin, carrageenan, and locust bean gum can be used, but they are difficult to adequately dissolve in melted xylitol. Gelatin requires two hours with stirring.

Alternatively, the composition may be formed by pressing powders of polyol crystals and one or more gums into a tablet with a tablet press. Xylitol grains of 50 to 350 microns are preferred. The grains may be granulated with a coating of gum on the outside, such as Danisco Xylitab 200 which is granulated with up to but less than 2% carboxymethylcellulose (CMC) as a compression binder. This is not enough CMC to achieve a preferred slow rate of dissolution. Adding at least 1.2% powdered CMC 15 from TIC Gums is effective. Adding 2.1% to 3.5% is preferred, depending on how much CMC is on the xylitol grains as a compression binder and the viscosities of both the CMC on the grains and the added powdered CMC. A 0.7 gram troche about 4.5 mm thick dissolved in 47 minutes in the mouth, nearly twice the minimum goal of 25 minutes, with 1.2% added CMC 15. With 2.5% added CMC 15, the dissolution rate was 90 minutes. With 3.5% added CMC 15, the dissolution rate was 120 minutes. A 0.5 gram troche with 3.4% low viscosity CMC dissolved in 40-120 minutes, depending on saliva flow.

Figure 2:
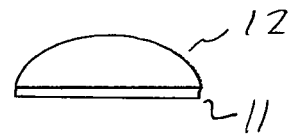
FIG. 2 shows a side view or cross section of a bi-layer adherent troche made by depositing a blob of paste onto a layer of adhesive material.
Figure 3:
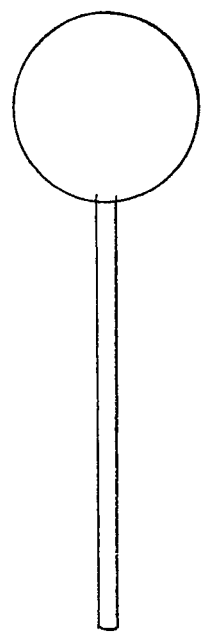
FIG. 3 shows a troche in the form of a lollipop.
Figure 4:
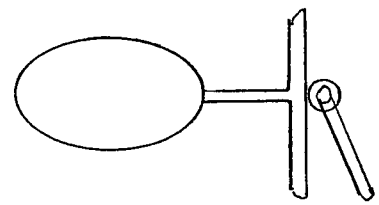
FIG. 4 shows a troche in the form of a child's pacifier.

Alternatively, grains of pure xylitol, such as Danisco Xylitab 300, may be mixed with gum powder and then pressed. Tested and found effective were 3% xanthan plus konjac gum with 0.5% high viscosity CMC, 10% alginate gum, 30% gelatin, 8% alginate with 8% gelatin, 11% acacia gum, 11% pectin, 14% guar gum, and 12% locust bean gum, The composition may be formed into a simple troche as shown in FIGS. 1 and 2, a troche with a handle to form a lollipop, as shown in FIG. 3, or a troche in the form of a child's pacifier, as shown in FIG. 4. Such a lollipop or pacifier may be used by a child younger than six without risk of aspiration of the troche. A suitable manufacturing method is the common method of making of lollipops by heating with kneading to a hot, slowly flowable paste, then forming onto the stick with use of molds, then cooling.

Alternatively, to achieve slow release of polyol molecules when added to other products held in the mouth, such as chewing gum, the composition may be formed into grains suitable for mixing into other foods, particularly foods with low water levels so that the grains do not dissolve into the foods. A suitable manufacturing method is the common method of granulating to form grains for tablet pressing, but adding more gums sufficient to achieve slow dissolution. A chewing gum embodiment may be made by coating fine grains of xylitol with 2.5%-6% carboxymethylcellulose (CMC) (by weight relative to the xylitol) and incorporating these grains into a chewing gum with insignificant amounts of water so the CMC remains un-hydrated until the gum is chewed.

The embodiment of an adherent troche that, when held in a human mouth, erodes, thereby releasing polyol molecules over time, allows delivery of polyol molecules without the effect on appearance of chewing or having a mint in one's mouth. It can also be used while sleeping. In a preferred embodiment, the dimensions and structure cause it to take more than 25 minutes to dissolve.

In preferred embodiments, the troche comprises, by dry weight between 50% and 90% solid phase polyol molecules, particularly xylitol. Lesser amounts are unattractive to the user who must consequently use more troches. Greater amounts are unachievable because at least 10% is needed for the adhesive and binders that hold it together and slow the release. This leaves between 10% and 50% for the adhesive molecules that adhere in a human mouth as well as binder molecules.

The adhesive molecules may comprise acacia gum. Acacia gum adheres very well to teeth and gingiva, which are the preferred locations for adhesion, and it does not dissolve too fast or leave an unattractive mouth feel. On the surface designed to be adherent, between 80% and 100% acacia gum is preferred for good adhesion. Alternatively, the adhesive molecules may comprise one or more of gelatin, alginate, starch, pectin, polyvinylpyrolidone, carboxymethylcellulose, hydroxymethylcellulose, polyvinyl acid, polyacrylic acid, and carbopol.

The adherent layer can be quite thin. In tests on a preferred size of troche, about 11.5 mm in diameter by 4 to 5 mm thick, the preferred thickness of a layer of about 99% acacia gum was about one-half millimeter. This can be made by bi-layer tablet pressing or by depositing a paste of acacia gum into a mold or by extrusion and die cutting.

The troche can be made as one homogenous composition, such as with highly adhesive molecules like the synthetics, polyvinylpyrolidone, carboxymethylcellulose, hydroxymethylcelluloSe, polyvinyl acid, polyacrylic acid, and carbopol at about 20 to 50%. Or, as show in FIG. 2, it may comprise two layers, a first layer 12 comprised of, by dry weight, at least 75% solid phase polyol molecules and a second layer 11 comprised of, by dry weight, at least 30% adhesive molecules. To minimize gums required and minimize size for the amount of polyol delivered, making a bi-layer troche is preferred.

As shown in FIG. 1, the preferred embodiment of the troche is made on a bi-layer tablet press, putting 85 to 95% of the total weight into a polyol layer 1 of about 90 to 97% polyol and 5 to 15% of the weight into an adhesive layer 2 of 30 to 99% adhesive gums. A pressed. powder bi-layer round xylitol troche, 12 mm in diameter and 4 to 5 mm thick with one-half millimeter of 99% acacia gum in one layer and 3.4% CMC gums in the xylitol as described above adheres well and dissolves in about 40-90 minutes, about double the minimum goal of exceeding 25 minutes.

When making bi-layer tablets with a typical press, a first powder is place in the die, sitting on the lower punch, then the upper punch tamps the powders, leaving the surface having the shape of the upper punch face, then powders of the second layer are added, then an upper punch presses again. To give the tablets a rounded upper surface and a flat lower adhesive surface where the adhesive has a uniform thickness, one must use two different upper punches, the first flat and the second dished, which can not be done on a typical bi-layer press.

A method for making a rounded bi-layer oral adhesive tablet on a typical bi-layer press is to configure the press to have a lower punch that is dish shaped to produce a rounded tablet surface and an upper punch that is substantially flat. One makes tablets with the press by first pouring into the die a granular material that is not intended to be oral adhesive, then tamping the granular material with the upper punch, then adding to the die oral adhesive granular material, then compressing the granular materials between the two punches to form a tablet that is substantially flat on an oral adhesive side and rounded on the other side.

The dish shape may be approximately a portion of a sphere. The dish shape may be produced by a face on a lower punch that is substantially flat in a center area and the center area is surrounded by a raised edge which forms a dish shape. For a troche 12 mm in diameter, a suitable amount of dish is 1.5 to 3 mm, preferably 2.1 mm, with a total tablet thickness of 4 to 5 mm.

Combating Bacterial Effects in the Oral-nasal Cavities

The compositions and troches described above may be used for combating bacterial effects in the oral-nasal cavities. Dissolving troches comprising crystalline xylitol which, when exposed to saliva in a human mouth, on average, release xylitol molecules more slowly than a troche of pure xylitol are supplied to consumers. The consumers are instructed to place a troche in their mouths and keep it there until the xylitol in the troche is dissolved. In one embodiment, the dissolution time of the troches in a human mouth is, on average, more than 25 minutes. The greater the number of hours each day with a troche releasing xylitol in the mouth, the better, up to a point of diminishing returns. Using one troche as described above at the end of each day and one after each meal, at least four per day, which adds up to two or more hours per day, is presently preferred. More studies are needed to determine preferred usage with greater precision.

The bacterial effects combated include oral malodor, inner ear infections, gum infections, caries, plaque, or sinus infections. For combating sinus infections, the method is effective with troches of pure xylitol or with xylitol chewing gum. That is, slower dissolution is not required, provided sufficient quantities of xylitol are delivered. Users adhere a troche to a tooth or adjoining gums in the rear of their mouths at any time of day or night, preferably after each meal or snack, at least four times per day. Placing it on the tongue side of the teeth causes it to erode more quickly than placing it on the cheek side. It can instead be adhered to the cheek.

Research shows that *Streptococcus* mutans in the blood is an important contributor to plaque in arteries and on heart valves. For people whose blood is not already infected with *Streptococcus* mutans, every day use of xylitol sufficient to suppress the *Streptococcus* mutans in the oral cavity will reduce their risk of subsequent cardiovascular disease.

While particular embodiments of the invention have been described above the scope of the invention should not be limited by the above descriptions but rather limited only by the following claims.

What is claimed:

1. A bi-layer, pressed powders, oral adhering tablet, comprising:
   a first layer comprising an adhesive powder, wherein the adhesive powder comprises at least 80% acacia gum; and
   a second layer comprising a powder containing an ingredient to be released into saliva in a mouth;
   wherein dissolution time of the tablet in the mouth is at least 25 minutes, and wherein the tablet is at least 5 mm in two dimensions;
   wherein the side of the tablet opposite the adhesive is either planar or rounded or substantially flat in a center area.

2. The tablet of claim 1, wherein the adhesive powder comprises about 99% acacia gum.

3. The tablet of claim 1 wherein the volume of the second layer is greater than the volume of the first layer.

4. The tablet of claim 1, wherein the tablet is substantially flat on an adhesive side and rounded on the opposite side.

5. The tablet of claim 1, wherein the ingredient comprises one or more polyols.

6. The tablet of claim 5, wherein at least one of the polyols is xylitol.

7. The tablet of claim 6, wherein the xylitol is present at a concentration of at least 75% in the second layer.

8. The tablet of claim 6, wherein the xylitol is present at a concentration of at least 90% in the second layer.

9. The tablet of claim 5, wherein the at least one polyol is present at a concentration of at least 90% in the second layer.

10. The tablet of claim 1, wherein the first layer is about 0.5 mm thick.

11. The tablet of claim 1, wherein the tablet is about 12 mm in diameter.

12. The tablet of claim 5, wherein the polyol comprises grains of powder.

* * * * *